United States Patent [19]
Metz-Stavenhagen

[11] Patent Number: 5,946,988
[45] Date of Patent: *Sep. 7, 1999

[54] TOOL FOR DRIVING PEDICLE SCREWS

[75] Inventor: Peter Metz-Stavenhagen, Bad Wildungen, Germany

[73] Assignee: Howmedica GmbH, Schoenkirchen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/681,783

[22] Filed: Jul. 29, 1996

Related U.S. Application Data

[63] Continuation-in-part of application No. 08/581,881, Jan. 2, 1996, abandoned, which is a continuation of application No. 08/481,233, Jun. 13, 1995, abandoned, which is a continuation of application No. 08/334,973, Nov. 7, 1994, abandoned, which is a continuation of application No. 08/023,491, Feb. 26, 1993, abandoned.

[30] Foreign Application Priority Data

Feb. 27, 1992 [DE] Germany .................. 92 02 561 U

[51] Int. Cl.⁶ .................................... B25B 13/28
[52] U.S. Cl. .................... 81/111; 81/93; 81/109
[58] Field of Search ................... 81/92, 97–99, 81/100, 106, 107, 109, 111–116; 606/104, 205

[56] References Cited

U.S. PATENT DOCUMENTS

| 1,153,050 | 9/1915 | Estes | 81/93 |
| 2,513,956 | 7/1950 | Ollaguon | 81/93 |

FOREIGN PATENT DOCUMENTS 2118474  11/1983  United Kingdom .

*Primary Examiner*—D. S. Meislin
*Attorney, Agent, or Firm*—Peter C. Richardson; Lawrence C. Akers; Elizabeth O. Slade

[57] ABSTRACT

A tool for driving pedicle screws into vertebrae of the human spine has a shaft preferably with a handle at one end and, at the opposite end, a holder for receiving a preferably ring-shaped head which is flattened on opposite sides. The tool has a first clamping jaw (18) secured to the shaft (12), and a second loose clamping jaw (20) including a lateral projection which is tiltably received by the first clamping jaw (18). The tool has an axially slidable actuating member (32) which is guided along the shaft (12). The front end of the actuating member (32) engages the rear end of the second clamping jaw (20) and is preferably axially urged towards the second clamping jaw (20) by a threaded driving means.

15 Claims, 9 Drawing Sheets

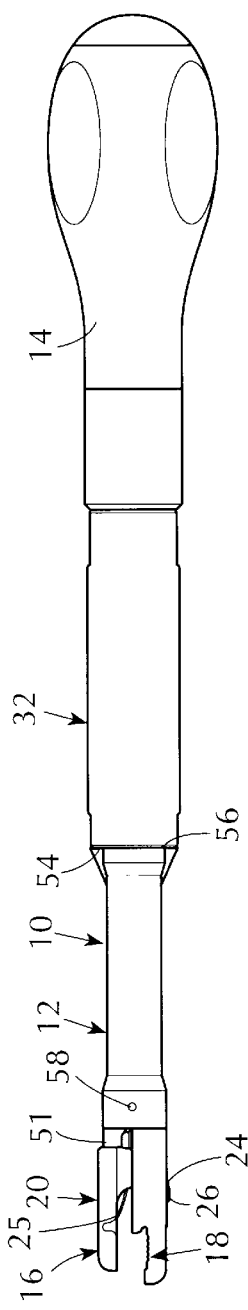
FIG. 1
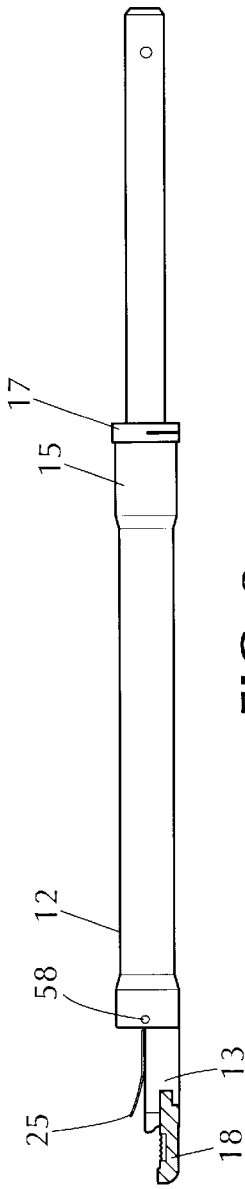
FIG. 2
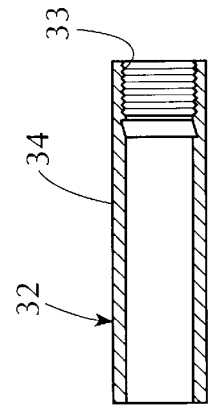
FIG. 5
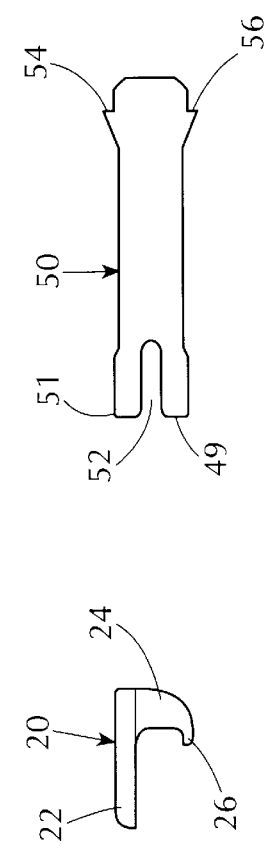
FIG. 4
FIG. 3

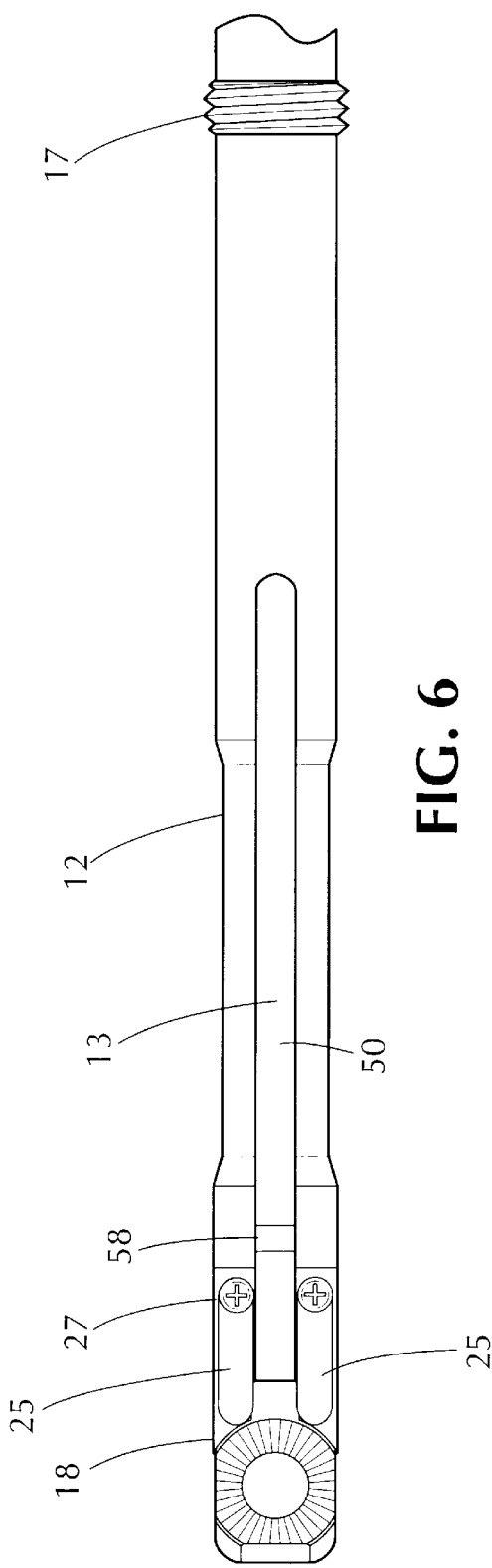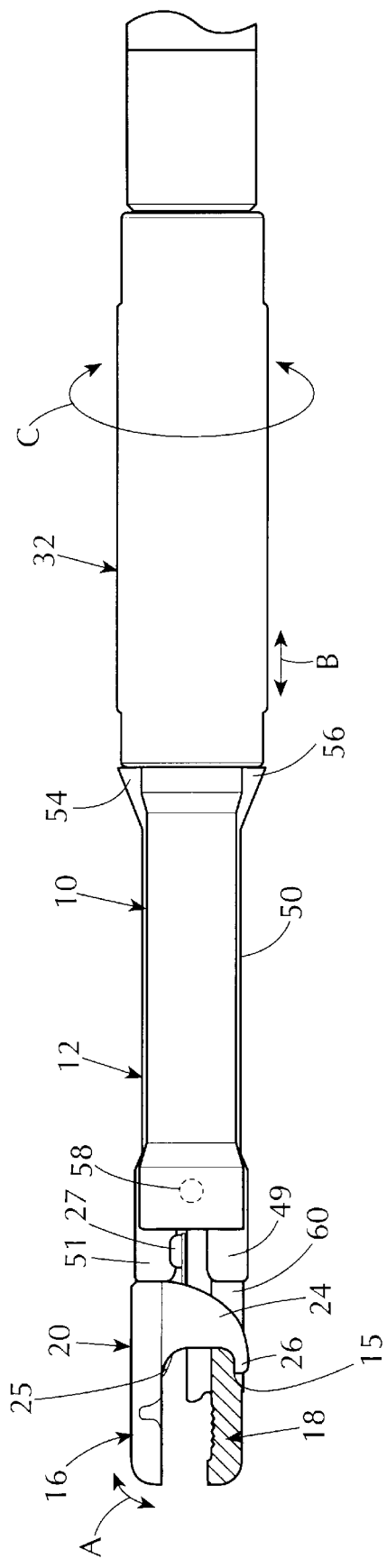
FIG. 6
FIG. 7

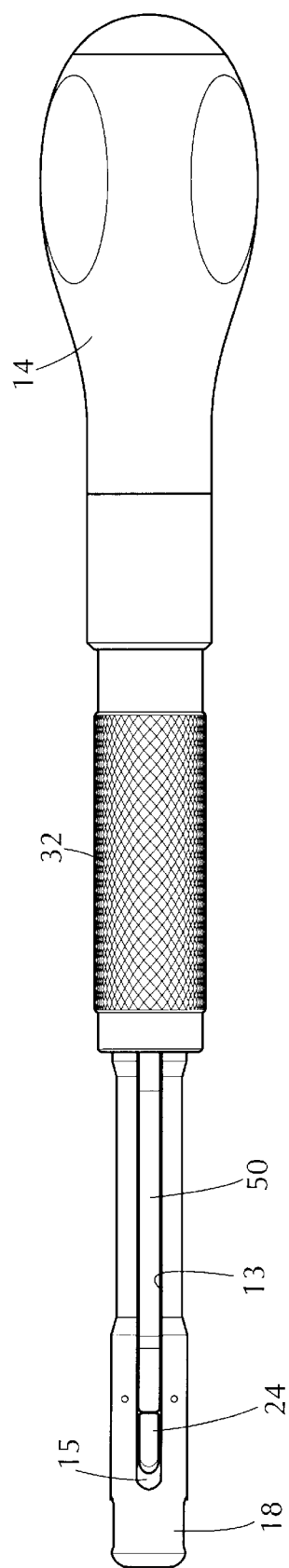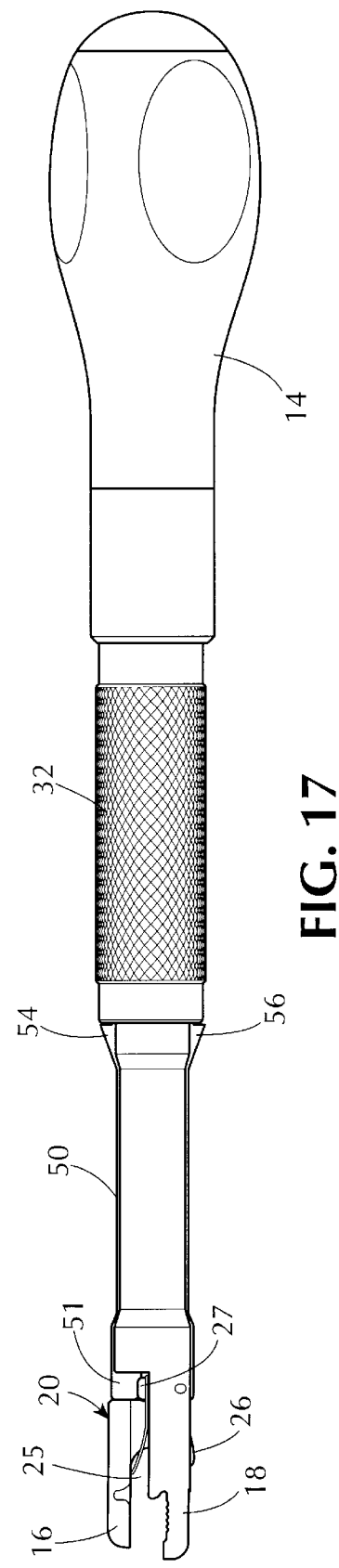

TOOL FOR DRIVING PEDICLE SCREWS

This application is a continuation-in-part of application U.S. Ser. No. 08/581,881, filed on Jan. 2, 1996 (now abandoned), which is a continuation of U.S. Ser. No. 08/481, 233, filed on Jun. 13, 1995 (now abandoned), which is a continuation of application Ser. No. 08/334,973, filed on Nov. 7, 1994 (now abandoned), which is a continuation of application Ser. No. 08/023,491 filed on Feb. 26, 1993, (now abandoned).

The present invention relates to a tool for driving pedicle screws.

So-called pedicle screws are screwed into the vertebrae of the human spine, i.e. in the pedicle area, to form substantial components to support the human spine, for example. Generally, pedicle screws are used to exert a force on the vertebrae for positioning them with respect to each other to give support or the like. In this connection a supporting means is disclosed in EP 0 328 883, in which at least a pair of pedicle screws is dorsally screwed into the vertebrae. The ring-shaped head end of the pedicle screws includes parallel clamping faces on opposite sides, including toothing, for example. Two pedicle screws are fixed at a distance apart by a clamping means including a pair of threaded bolts which cooperate with a threaded sleeve having reverse threaded portions.

For driving pedicle screws into the vertebrae in the pedicle areas, a high skill of the surgeon is necessary since the available space is small. The driving operation requires a tool which is suited to safely receive the substantially ring-shaped head of the pedicle screws and to transfer the driving force onto the screw.

It is thus an object of the present invention to provide a tool for driving pedicle screws into the vertebrae of the human spine, which tool is easily operable, affords an easy clamping and removing of these pedicle screws and, moreover, ensures the application of the driving force necessary.

The objects are solved by the device of the invention.

SUMMARY OF THE INVENTION

According to the invention, a first clamping jaw is rigidly connected to a tool shaft. A second loose clamping jaw is tiltably held by the first jaw so that it can be pivoted with respect to the first clamping jaw. An axially slidable actuating member is guided along the shaft, the front end of the member contacting the rear end of the second clamping jaw and urged towards the second clamping jaw by a thread driving means or the like.

According to the invention the loose clamping jaw may perform a tilting motion as well. This is initiated by urging the actuating member towards the rear end of the clamping jaw so that the head of the pedicle screw received between the clamping jaws is tightly clamped between the clamping jaws to be subjected to the necessary driving force.

According to an embodiment of the invention, the first clamping jaw includes a through-going guiding recess, and the projection is defined by a hook-shaped portion contacting the outer side of the first clamping jaw. The recess has an axial length to accommodate the hook-shaped portion in dismounting.

According to the invention, a particularly simple embodiment of the actuating member comprises a sleeve which is axially slidable along the shaft to engage the rear side of the movable jaw. The sleeve may be displaced by a further sleeve, for example, which threadably engages the shaft to apply an axial force to the sleeve when being rotated. According to an embodiment of the invention the sleeve includes an internal threaded portion cooperating with a threaded portion of the shaft. To simply actuate the sleeve, an embodiment of the invention provides an enlarged and preferably knurled portion thereon.

According to a still further embodiment of the invention a spring is arranged between the clamping jaws to urge the jaws apart to facilitate receiving and releasing the head of the pedicle screw.

The opposite flatened sides of the pedicle screw head are often roughened or toothed. The clamping faces of the jaws are thus preferably formed correspondingly.

The tool according to the invention provides a movable or, respectively, loose clamping jaw which is slidable (for dismounting) as well as tiltable. However, the scope of protection includes an embodiment in which the movable jaw is tiltably mounted merely about an axis passing through the stationary clamping jaw.

According to a further embodiment a thrust member is axially slidably mounted on the shaft to engage the movable clamping jaw, whereas the actuating sleeve cooperates with the thrust member. As the sleeve is displaced towards the handle, the front portion of the tool becomes slimmer.

The movable clamping jaw may be provided with a surface extending under a predetermined angle to afford a clamping of angular screws having a flat head.

DESCRIPTION OF THE PREFERRED EMBODIMENTS

A preferred embodiment of the invention will now be described with reference to the accompanying drawings which show FIG. 1 a side view of a tool according to the invention, FIG. 2 a side view of the shaft for the tool of FIG. 1, FIG. 3 a movable clamping jaw for the tool of FIG. 1, FIG. 4 a thrust member for the tool of FIG. 1 and FIG. 5 an actuating sleeve for the tool of FIG. 1.

FIG. 6 is a plan view of the device shown in FIG. 2, viewed from above, showing the slot 13 in the shaft in which the thrust member 50 (also shown in FIG. 4) is positioned (as shown in FIG. 1). Springs 25 with attachment screws 27 and pin 58 are also shown.

FIG. 7 is a part of FIG. 1 drawn at a larger scale and wherein the front part of clamping jaw 18 is shown in cross-section.

FIGS. 16–19 are drawings showing intervals of 90° of the device of the invention with its four main parts assembled together, those parts including the shaft, the movable jaw having a curved hook shape, the threaded cylinder, and the plate-shaped thrust member. The four photographs were taken with no change having been made to the device of the invention except that the device was moved with respect to the camera. The device is shown in its open position (as opposed to its closed position shown in FIGS. 20 and 21).

Figure 20:
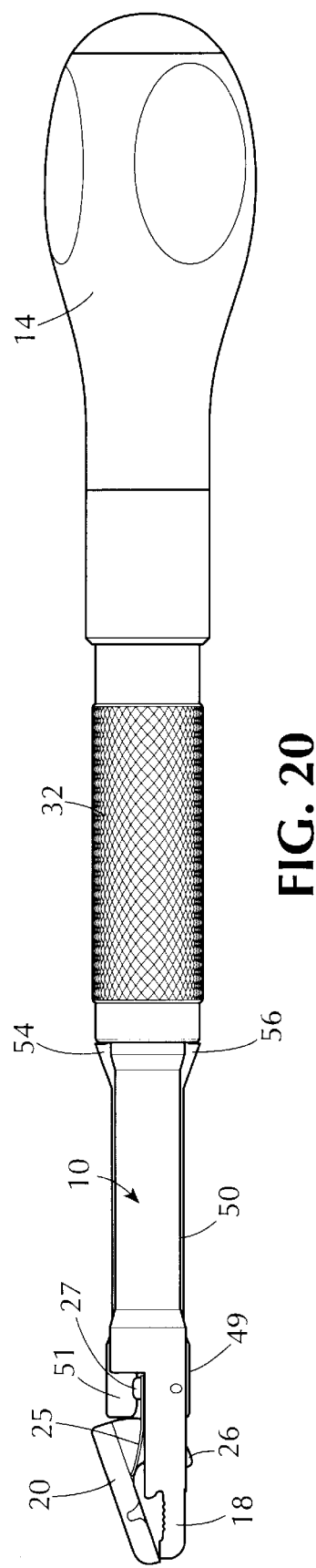
Figure 21:
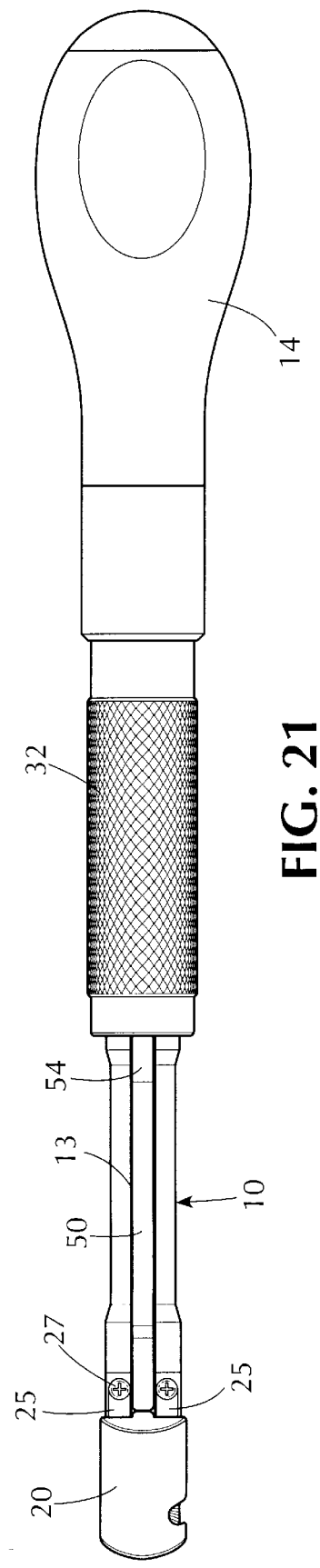

FIGS. 20 and 21 are drawings showing taken at an interval of 90° of the driver according to the invention with its four main parts assembled together, showing the driver in its closed position with its movable jaw moved as closely as possible toward its fixed jaw.

FIG. 1 shows a screw driver 10 for pedicle screws, comprising a shaft 12 at one end of which a handle 14 and at the other end of which a receiving and clamping portion 16 are provided. A fixed clamping jaw 18 is rigidly secured to the shaft 12 to cooperate with a movable clamping jaw 20. The movable clamping jaw 20 is shown in FIG. 3. It comprises a clamping portion 22 and a lateral projection 24 at the rear which is shaped like a hook at 26. The lateral projection 24 extends through an elongated opening (not shown) in the fixed jaw 18. A spring 25 is positioned so as to urge the jaws 18 and 20 apart.

FIG. 4 shows a plate-like thrust member 50 having an open slot 52 at the front end and a pair of shoulders 54, 56 at the rear end. A pin 58 extends across the shaft 12, said pin extending through the slot 52 of the thrust member 50 when the thrust member 50 is received in a slot 13 (shown in FIG. 6) in the shaft 12.

FIG. 5 shows a sleeve 32 including an inner thread 33. An enlarged end portion of the shaft 12 includes a threaded portion 15 including a flange 17 from which a more slender portion extends rearwardly receiving the handle 14. The threaded portion 33 of the sleeve 32 cooperates with the threaded portion 15 of the shaft 12, whereas the right end of the thrust member 50 as shown in FIG. 4 extends through the sleeve 32 when the parts are mounted on the shaft 12 according to FIG. 1, wherein the shoulders 54, 56 contact the adjacent end of the sleeve 32. The outer surface of sleeve 32 is a knurled portion 34, shown in FIG. 5.

The head of a pedicle screw (not shown) is received in the mouth of the clamping jaws 18, 20, wherein FIG. 1 shows the receiving position. When the sleeve 32 is rotated it is displaced forwardly and moves thus the thrust member 50 to the front end to engage the rear end of the movable jaw 20. It tilts forwardly and thus urges the head of the pedicle screw towards the fixed clamping jaw 18. Thereby the head of the pedicle screw is safely held in the tool 10 and may be screwed into a vertebra. After screwing-in, the sleeve 32 is counter-rotated so that the tool may be removed by releasing the head of the pedicle screw.

As shown, the tilting axis is located outside the axis of the shaft 12. The contact point of the movable clamping jaw 20 is axially off-set alike so that the clamping jaw 20 is subjected to a torque anti-clockwise to thus approach the front region of the clamping jaw 18. This geometry is used to apply the clamping force mentioned before.

By correspondingly modifying the clamping face of the movable jaw 20, for example by an angular face in the front area, angular screws having a flat head may be clamped as well.

It should be understood that the thrust member 50 may be eliminated when the sleeve 32 directly engages the movable clamping jaw 20. In this embodiment the front portion of the tool is thicker which could be objectionable because of a worsened view.

FIG. 6 is a plan view of the device shown in FIG. 2, viewed from above, showing the slot 13 in the shaft 12, in which the thrust member 50 (shown in FIG. 4) is positioned and centered (as shown in FIG. 1). Spring 25 with attachment screws 27 and pin 58 are also shown.

FIG. 7 is a part of FIG. 1 drawn at a larger scale and wherein the front part of clamping jaw 18 is shown in cross-section. Shown are two prongs 49 and 51 and shoulders 54 and 56 of thrust member 50 (which is also shown in FIG. 4). The lateral projection 24 (of movable clamping jaw 20) extends through an elongated opening 60 in the fixed jaw 18. Elongated opening 60 is preferably a continuation of slot 13. As can be seen in FIG. 1 the hook portion 26 of projection 24 engages with a portion of fixed jaw 18. Hook portion 26 grips a portion of the lower side of fixed clamping jaw 18. Movable jaw 20, thus, may pivot as indicated by double-arrow A.

As can now be clearly seen in FIG. 7, the rear edge of projection 24 is rounded. Thus, a space 60 is left between the lower prong 49 of the bifurcated thrust portion 50 and projection 24, even when the upper prong 51 of thrust member 50 engages jaw 20. From FIG. 7, it is also clear that movable jaw 20 may tilt with respect to fixed jaw 18 when thrust member 50 is axially moved. In other words, an axial movement of thrust element 50 (indicated by double-arrow B) such that prong 51 thereof engages movable jaw 20 leads to a tilting of jaw 20. The axial movement of thrust element 50 (indicated by double-arrow B) is achieved by an axial movement of sleeve 32. This axial movement of sleeve 32 is achieved by turning sleeve 32 (as indicated by double-arrow C). The threads of sleeve 32 interengage with the threads of shank 12 (see FIG. 5 and FIGS. 8–11). Thus, movable jaw 20 pivots about the point where the end of hook portion 26 grips the lower side of fixed clamping jaw 18.

Figure 8:
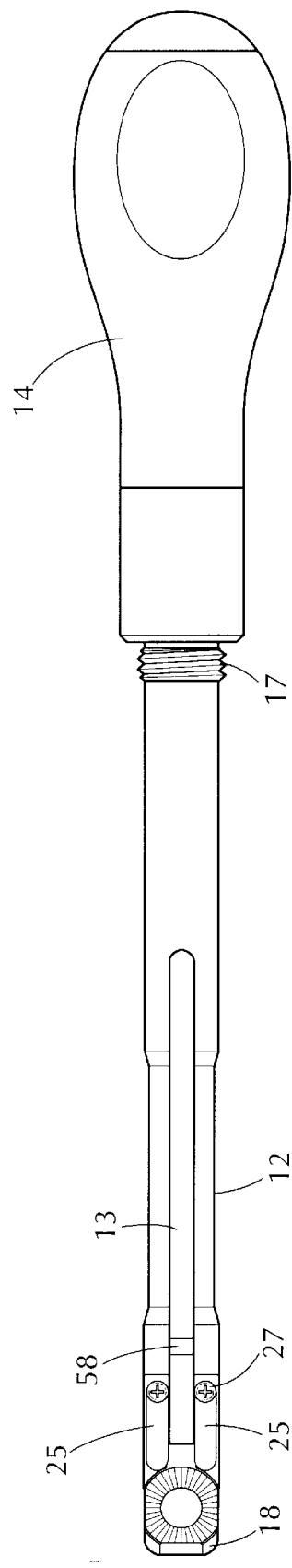
FIGS. 8–11 are drawings showing consecutive intervals of 90° of the shaft which has a long slot into which a thrust member is to be positioned and centered and which also includes a fixed first jaw rigidly attached to the shaft at one end thereof and a handle rigidly attached to the shaft at the other end thereof.
Figure 9:
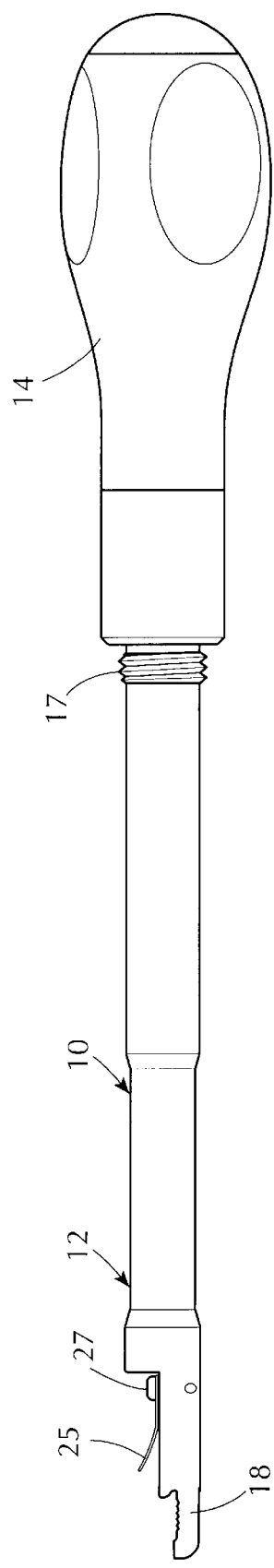
Figure 10:
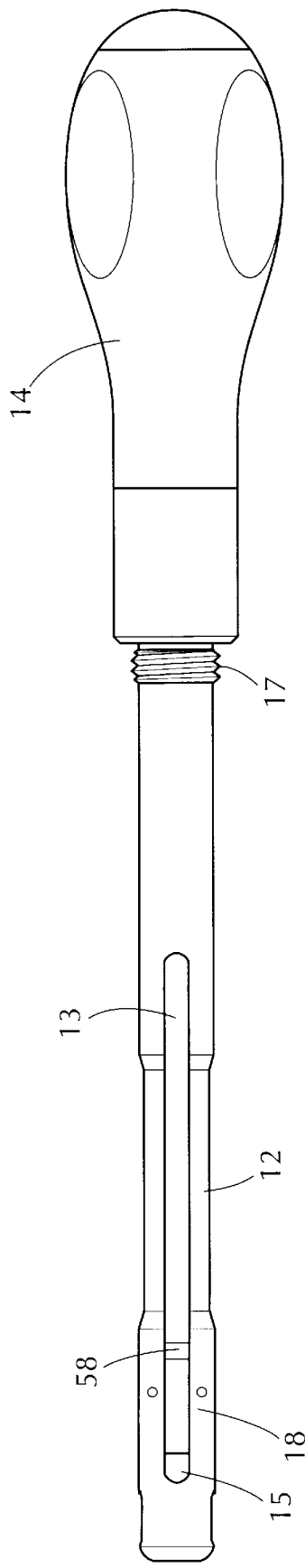
Figure 11:
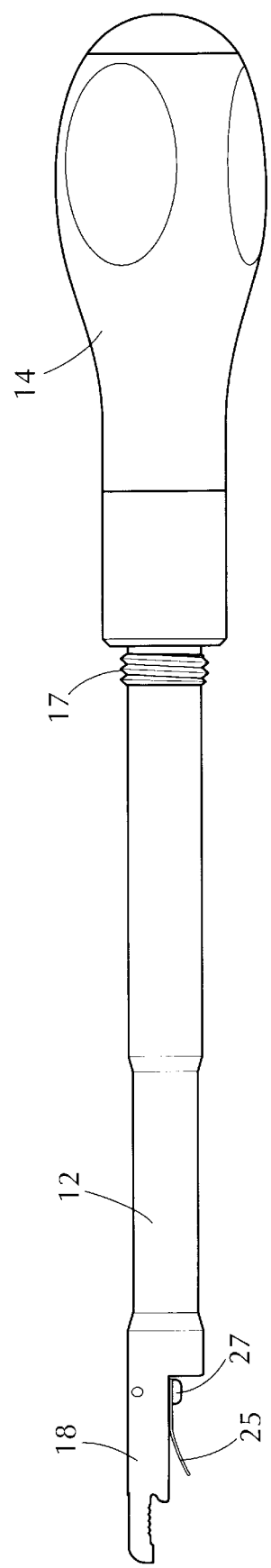
Figure 12:
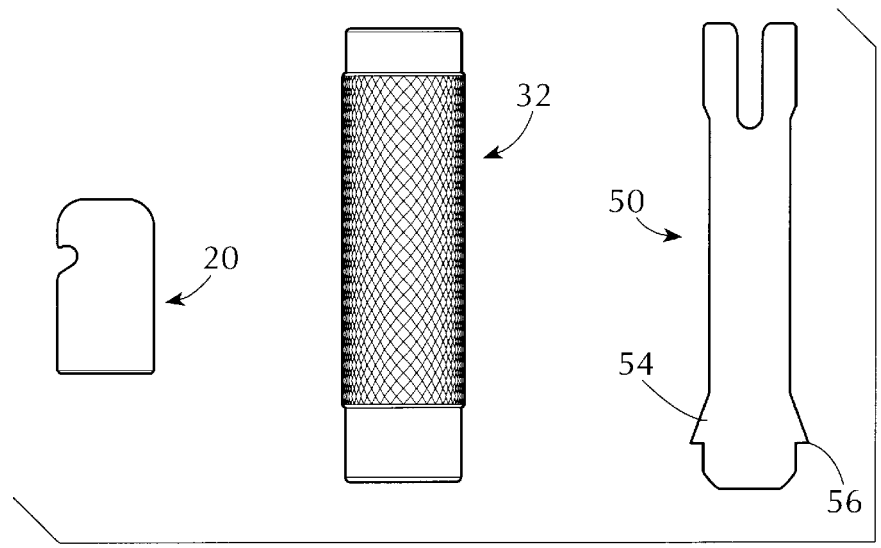
FIGS. 12 and 13 are drawings of the three additional main parts of the device of the invention which are to be attached to the shaft. The three removable main parts include (1) a second (movable) jaw having a curved hook shape, (2) a threaded cylinder, and (3) a plate-shaped thrust member having two shoulders near one end thereof and having two prongs at the other end thereof.
Figure 13:
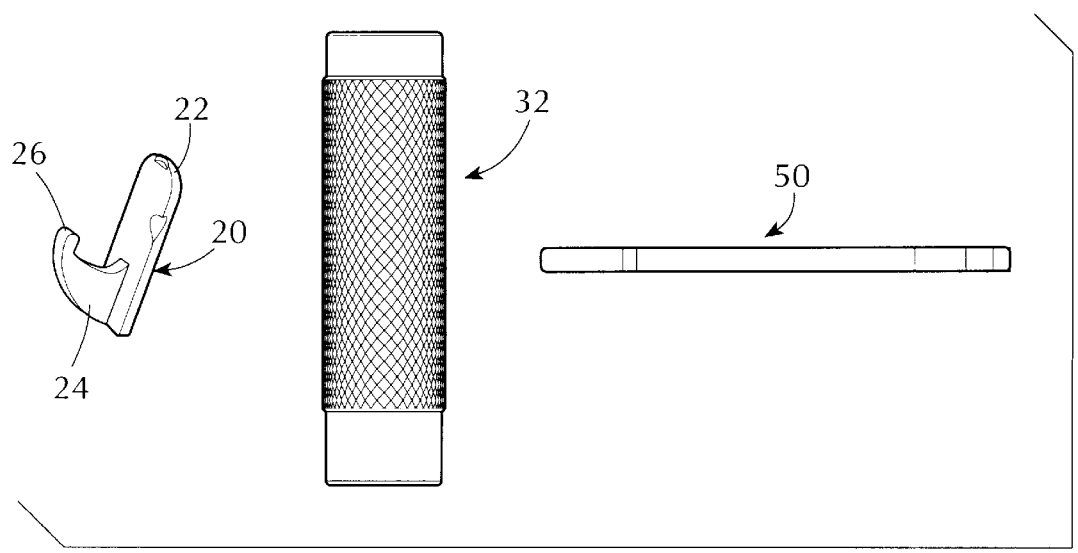
Figure 14:
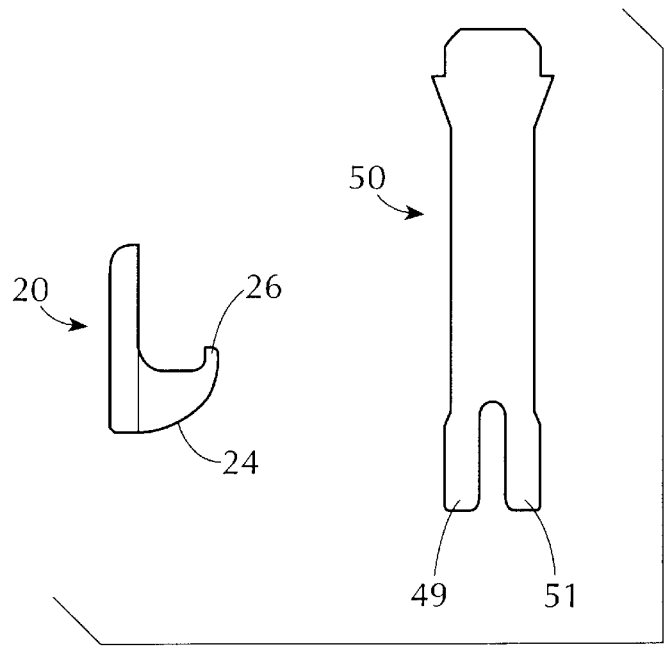
FIGS. 14 and 15 are drawings showing intervals of 90° of the hook-shaped movable jaw and the plate-shaped thrust member.
Figure 15:
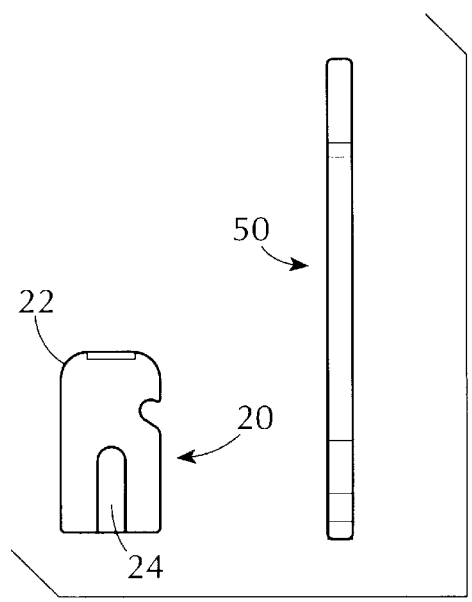
Figure 18:
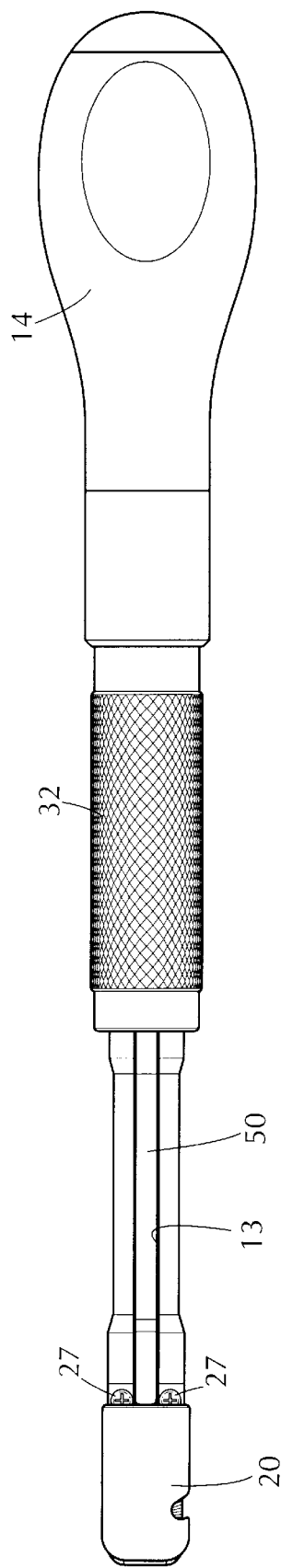
Figure 19:
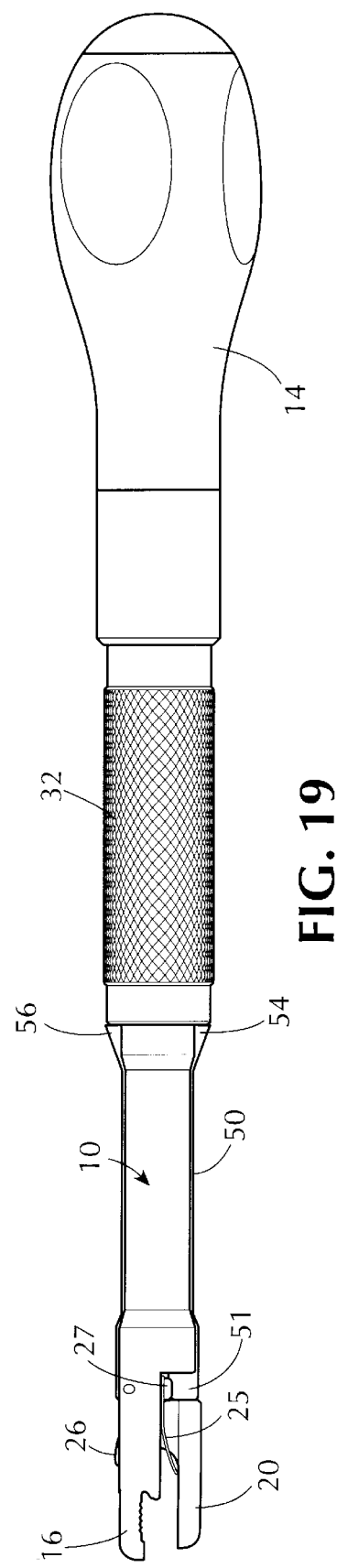

In assembling the four main parts (described above) of the device of the invention together, the following procedure will be carried out. As shown in FIG. 8, the shaft 12 with handle 14 attached thereto has a threaded portion 33 (see FIG. 5) which is threaded with the threads of sleeve 32. Next, thrust portion 50 is inserted into slot 13 and adjusted so that prongs 49 and 51 of the bifurcated portion fit with pin 58 located within open slot 52. Then, the rear portion (shaped like a hook 26) of lateral projection 24 is inserted into an elongated opening 60 (which is connected with slot 13) in fixed clamping jaw 18, and hook portion 26 engages and grips the lower side of fixed clamping jaw 18 at opening 15 (shown at FIGS. 10 and 16). Next, threaded sleeve 32 is moved so that thrust portion 50 engages movable jaw 20 at prong 51 of thrust member 50. Movable jaw 20 tilts, and jaw 20 and jaw 18 are in their closed position (as seen in FIGS. 20 and 21). A pedicle screw will be able to be firmly clamped between jaws 18 and 20 in the device of the invention.

I claim:

1. A tool for driving pedicle screws into a vertebra of the human spine, comprising a shaft having a handle at one end and at the opposite end having a holder for receiving a ring-shaped head of a pedicle screw, which head is flattened on opposite sides, wherein said holder comprises a first clamping jaw (18) and a second clamping jaw (20), wherein said first clamping jaw (18) is secured to the shaft (12), wherein said second clamping jaw (20) is movable and includes a lateral projection (24) which is tiltably received by the first clamping jaw (18) and wherein an axially slidable actuating member (50) is guided along the shaft (12), wherein said actuating member engages said second clamping jaw (20) so as to urge said second clamping jaw (20) to tilt toward said first clamping jaw by a thread driving means, wherein the first clamping jaw (18) includes a slot (13) and wherein said projection (24) includes a hook-shaped portion (26) engaging said first clamping jaw (18).

2. A tool of claim 1, wherein said thread driving means includes an axially slidable sleeve (32) mounted on the shaft (12) to be brought in engagement with said actuating member (50).

3. A tool of claim 2, wherein the sleeve (32) includes an inner threaded portion cooperating with a threaded portion of the shaft (12).

4. A tool of claim 3, wherein the sleeve (32) includes a knurled portion (34).

5. A tool of claim 4, wherein a spring (30) is mounted between the clamping jaws (18, 20) to urge the clamping jaws apart.

6. A tool of claim 5, wherein an actuating member is axially slidably mounted in the shaft, which actuating member coacts with the second clamping jaw (20), wherein the sleeve (32) cooperates with the rear end of the actuating member.

7. A tool for driving a pedicle screw into a vertebra of the human spine, said tool comprising:
 (a) a shaft having a first end and a second end;
 (b) a holder for receiving a head of a pedicle screw, said holder being located at said second end of said shaft, said holder comprising:
  (1) a first clamping jaw substantially rigidly secured to said shaft and
  (2) a movable second clamping jaw having a projection which is tiltably received by said first clamping jaw; and
 (c) an actuating member which is axially movable along said shaft and engageable with said second clamping jaw so as to tilt said second clamping jaw toward said first clamping jaw wherein said first clamping jaw includes a guide recess and wherein said projection includes a hook-shaped portion for engaging said first clamping jaw.

8. A tool according to claim 7, wherein said actuating member is slidably mounted on said shaft so as to be able to be brought into engagement with said second clamping jaw.

9. A tool according to claim 8, and including a driving means for driving said actuating member into engagement with said second clamping jaw wherein said driving means includes an inner threaded portion for cooperating with a threaded portion of said shaft.

10. A tool according to claim 9, wherein said driving means includes a knurled portion.

11. A tool according to claim 10, and including also a spring mounted between said first clamping jaw and said second clamping jaw for urging said first clamping jaw and said second clamping jaw apart.

12. A tool according to claim 11, wherein said actuating member is axially slidably mounted on said shaft such that said actuating member can coact with said second clamping jaw and wherein said actuating member cooperates with said driving means.

13. A tool for driving a pedicle screw into a vertebra of a human spine, said tool comprising:
 (a) a shaft having a first end and a second end and a slot therewithin;
 (b) a holder for receiving a head of a pedicle screw, said holder being located at said first end of said shaft, said holder comprising:
  (1) a first clamping jaw into which said slot extends and having a receptacle (15) therein and being substantially rigidly secured to said shaft and
  (2) a movable second clamping jaw having a hook-shaped curved projection which is tiltably received within said slot in said first clamping jaw and said projection having an end which fits securely within said receptacle in said first clamping jaw but permits rotation of said curved projection within said receptacle with respect to said first clamping jaw; and
 (c) a plate-shaped thrust member having a first extension extending therefrom and being axially movable within said slot located longitudinally within said shaft and being engageable at said first extension with said second clamping jaw at a single point on said curved projection so as to tilt said second clamping jaw with respect to said first clamping jaw so as to cause said holder to close and to be able to grasp said pedicle screw firmly.

14. A tool according to claim 13 and including also a driving means for driving said extension of said thrust member into engagement with said second clamping jaw at said single point on said curved projection.

15. A tool according to claim 14 and including also a handle located at said second end of said shaft, and wherein said driving means is a threaded cylinder having a first end which engages said second end of said thrust member and having a second threaded end which threads with threads on said shaft adjacent to said handle.

* * * * *